(12) United States Patent
Mock et al.

(10) Patent No.: US 8,399,529 B2
(45) Date of Patent: Mar. 19, 2013

(54) METHOD OF HOMOGENIZATION AND, OPTIONALLY, ANALYSIS FOR PROCESSING MOIST NOBLE METAL-CONTAINING RECYCLING MATERIALS WITH AN UNKNOWN NOBLE METAL CONTENT

(75) Inventors: Christian Mock, Shanghai (CN); Horst Meyer, Altenstadt (DE); Matthias Grehl, Frankfurt (DE); Jochen Schleβmann, Blankenbach (DE); Martin Stettner, Altenstadt (DE)

(73) Assignee: W.C. Heraeus GmbH, Hanau (DE)

( * ) Notice: Subject to any disclaimer, the term of this patent is extended or adjusted under 35 U.S.C. 154(b) by 133 days.

(21) Appl. No.: 11/470,659

(22) Filed: Sep. 7, 2006

(65) Prior Publication Data

US 2007/0065353 A1 Mar. 22, 2007

(30) Foreign Application Priority Data

Sep. 9, 2005 (DE) .................. 10 2005 043 286
Oct. 14, 2005 (DE) .................. 10 2005 049 702

(51) Int. Cl.
*C08J 11/04* (2006.01)

(52) U.S. Cl. .............. 521/40; 423/22; 423/76; 423/139; 423/140; 528/490; 528/502 R; 209/3; 209/12.1

(58) Field of Classification Search .............. 528/271, 528/272, 490, 502 R; 423/22, 76, 139, 140; 521/40, 40.5, 41, 41.5, 42, 42.5, 43, 43.5, 521/44, 44.5, 45, 45.5, 47, 47.5, 48, 48.5, 521/49, 49.5, 49.8; 209/3, 12.1
See application file for complete search history.

(56) References Cited

U.S. PATENT DOCUMENTS

| | | | |
|---|---|---|---|
| 5,403,566 A * | 4/1995 | Panster et al. .............. 423/22 |
| 5,939,086 A | 8/1999 | Levy | |
| 6,623,645 B1 | 9/2003 | Roach et al. | |
| 2004/0232068 A1 | 11/2004 | Johnston et al. | |
| 2005/0014912 A1* | 1/2005 | Hirota et al. ............... 526/90 |

FOREIGN PATENT DOCUMENTS

| | | |
|---|---|---|
| DE | 199 42 519 | 6/2001 |
| DE | 101 30 808 A1 | 4/2002 |
| WO | 89 04475 | 5/1989 |
| WO | WO 96/39823 | 12/1996 |
| WO | WO 03/038405 A1 | 10/2002 |
| WO | 2005 058453 | 6/2005 |

OTHER PUBLICATIONS

Cullinane et al, "Handbook of Stabilization/Solidification of Hazardous Waste", EPA/540/2-86/001, Jun. 1986, pp. 2-1 to 2-9.*
Hagelueken C. et al; "Substantial outflows of platinum group metals identified spent autocatalysts are systematically withdrawn from the European market" ERZMETALL 56 (2003) No. 9; pp. 529-540.

* cited by examiner

*Primary Examiner* — Francis Tischler
(74) *Attorney, Agent, or Firm* — Norris McLaughlin & Marcus, P.A.

(57) ABSTRACT

For processing of noble metal-containing, moist recycling materials with an unknown noble metal content (hereinafter called "batch"), a moisture-binding agent is added for homogenisation and the batch is mixed with comminution of optionally pre-sent agglomerates to form a free-flowing and homogenous powder. Optionally, the following takes place subsequently for analysis:
A at least one representative, volume-reduced sample is taken first of all,
B the sample is dried,
C the sample is optionally divided further and
D the sample is analyzed and the noble metal content of the batch is calculated on the basis of the data
a previously known or pre-calculated quantity of the moisture-binding agent being added before sampling (step A).

17 Claims, 1 Drawing Sheet

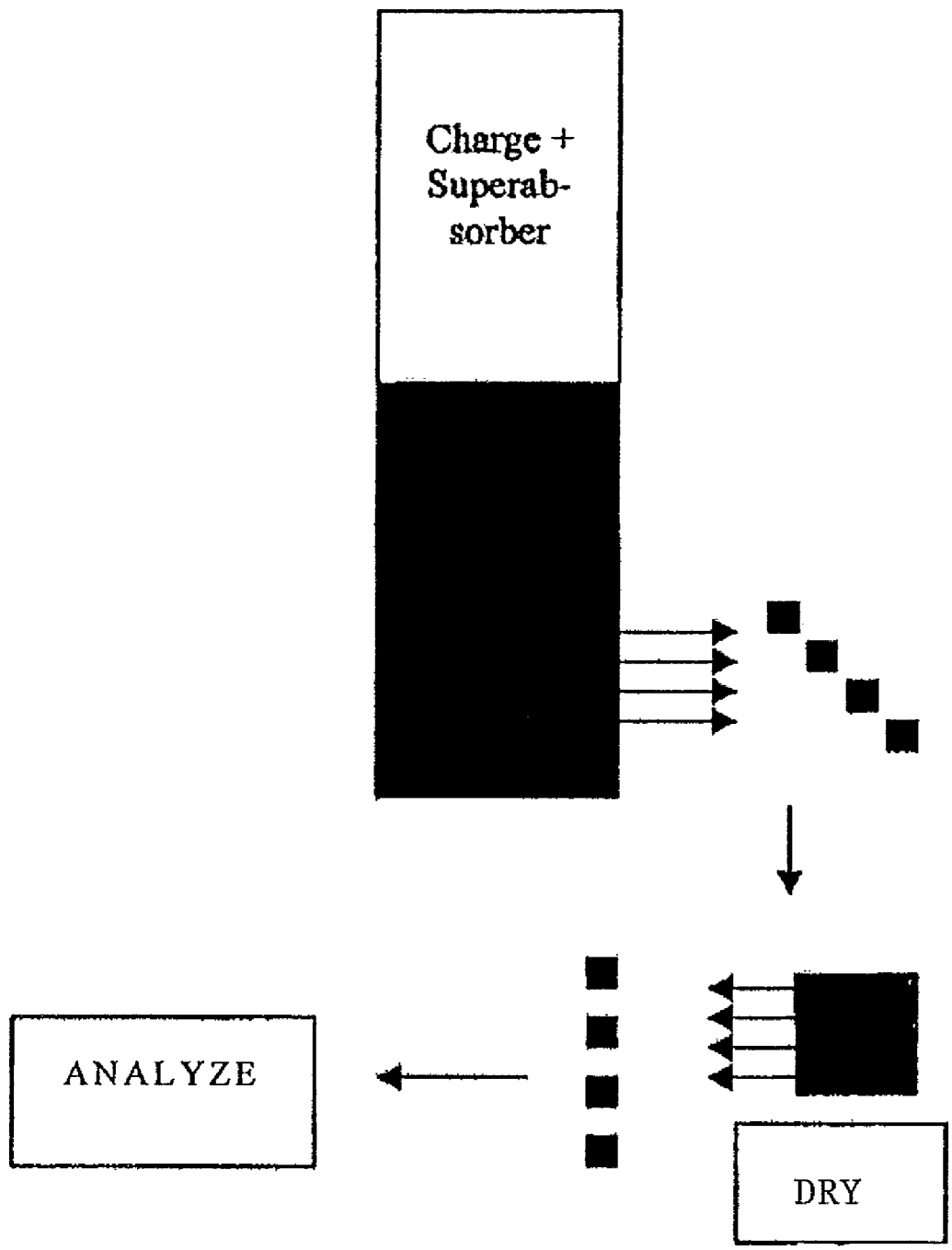

METHOD OF HOMOGENIZATION AND, OPTIONALLY, ANALYSIS FOR PROCESSING MOIST NOBLE METAL-CONTAINING RECYCLING MATERIALS WITH AN UNKNOWN NOBLE METAL CONTENT

The invention relates to a method of homogenization and/or analysis for processing noble metal-containing, moist recycling materials with an unknown noble metal content (hereinafter called "batch"), in particular spent catalysts.

According to the patent application WO 03/038405 A1 (Johnson Matthey), there is a requirement for an improved method of sampling and analysis of waste products containing valuable substances. It is suggested therein to disperse the waste in a liquid and to withdraw a small portion of the mass continually for analysis.

It has been found that, by means of moisture-binding agents, the moisture in the batches supplied can be bound to such an extent that they can be homogenized in an almost dry state by means of suitable mixing and comminution devices.

The invention consequently relates to a method of homogenization for processing noble metal-containing, moisture-containing recycling materials with an unknown noble metal content (hereinafter called "batch"), characterized in that a moisture-binding agent is added and the batch is mixed with comminution of optionally present agglomerates to form a free-flowing and homogenous powder. A relatively dry, free-flowing powder is formed. Subsequently, an intermediate sample can be taken which can be divided into the individual final samples after a drying process.

For the analysis, the quantity of moisture-binding agent is previously known or pre-calculated such that, after analysis, the actual content of valuable substances of the waste supplied is determined.

The invention consequently also relates to a method of homogenization and analysis for processing noble-metal containing, moisture-containing recycling materials with an unknown noble metal content (hereinafter called "batch"), A one or several samples being taken first of all,
B the sample(s) being dried,
C the sample(s) being optionally divided further, and
D the sample(s) being analyzed and the noble metal content of the batch being calculated on the basis of the data characterized in that, before sampling (step A), a previously known or pre-calculated quantity of a moisture-binding agent is added and the batch is mixed with comminution of optionally present agglomerates to form a free-flowing and homogenous powder.

Moreover, the invention relates to advantageous embodiments of both methods as described in greater detail hereinbelow.

In a preferred embodiment, a previously known and/or pre-calculated quantity of a water-binding agent, e.g. an organic polymer, in particular a cross-linked polyacrylate or a so-called super-absorber is added to the batch supplied.

The purpose is to bind the moisture and/or water contents of the batch, which may amount from approximately 20 to 80%, as far as possible.

The method relates in a particularly preferred embodiment to carbon-containing catalyst residues (hereinafter called "carbon") which are supplied in the moist state. The material needs to be analyzed for the supplier to be informed of the content of valuable substances. The material needs to be as homogenous as possible for sampling.

One or several samples is/are taken from the mixture preferably during the agitation or mixing process.

Appropriately, the mixture is mixed intensively in a mixer with cutting rotors.

The intermediate sample(s) removed is/are appropriately dried, if necessary combined and further divided, e.g. by means of rotary dividers. The dried samples have a particle size of preferably <500 pm, particularly preferably <100 pm.

Following the analysis which takes place according to methods known as such, the samples taken can be passed to noble metal recycling together with the remaining batch.

The moisture may have been caused by water and/or organic solvents.

In the case of organic solvents, activated carbon, for example, is suitable as moisture-binding agent. If the moisture is water, usual water-binding agents such as zeolites are suitable. Preferably, so-called super-absorbers are used as water-binding agents.

Super-absorbers are weakly cross-linked, insoluble polymers which are capable of absorbing a multiple of their weight of water or aqueous solution. They swell up strongly during this process, a "hydrogel" is formed. All cross-linked polymers containing sufficient polar groups are capable of forming hydrogels, e.g. polyacrylamide, polyvinylpyrrolidone and natural polymers such as amylopectin, gelatine and cellulose. Thus, starch-acrylonitrile graft polymers are used. Polymers with ionic groups are capable of absorbing a particularly large amount of water since they assume a stretched form as a result of repulsion between the individual (identically charged) ionic groups. The water molecules are thus able to group themselves particularly well around the ions and to stabilize their position by reciprocal actions such as hydrogen bridges and arrangement of the dipoles.

If copolymers of acrylic acid (propenoic acid, $C_3H_4O_2$) and sodium acrylate (sodium salt of acrylic acid, $NaC_3H_3O_2$) are involved, it being possible for the ratio of the two monomers to each other to vary, a so-called core cross-linker (CXL) is added to the monomer solution, which cross-linker bonds the long-chain polymer molecules formed among each other at specific locations by chemical bridges ("cross-links" them). As a result of these bridges, the polymer becomes insoluble in water. On penetration of water or aqueous salt solutions into the polymer particle, it swells up and tightens this network at molecular level—the water can no longer escape unaided.

According to the present day state of development, the product in this form is referred to as "base polymer" since the requirements regarding the super-absorber have risen in the course of the years and further improvement steps are applied. The so-called surface cross-linking (SXL) deserves to be mentioned as the most important one. During this process, a further chemical is applied onto the surface of each particle and by way of a reaction taking place under heat, a second network is attached onto the outer layer of the grain exclusively. This prevents the solution absorbed from escaping by a tightening occurring also on liquid absorption even under pressure.

For the purposes of the invention, the super-absorbers of the first generation, however, are sufficient. However, since the use of production waste containing super-absorber may also be envisaged, super-absorbers of a newer generation can also be used in this way.

The super-absorbers can also be used in mixture with activated carbon.

BRIEF DESCRIPTION OF THE DRAWINGS

The invention will now be described in greater detail with reference to the drawings, wherein:

FIG. 1 is diagrammatic representation of an exemplary embodiment of the present invention.

EXAMPLE

FIG. 1 shows a diagrammatic representation of an exemplary embodiment of the process. Noble metal-containing, spent catalyst with an unknown noble metal content ("batch") is mixed with a defined quantity of super-absorber and individual samples are taken. The combined individual samples are dried, divided again and analyzed. The dried samples have a particle size of <100 pm. By the quantity of super-absorber for absorbing the water having been pre-calculated and being known, the noble metal content of the sample can be calculated.

What is claimed is:

1. Method of homogenization for processing noble metal-containing, moisture-containing recycling materials wherein the noble metal content is unknown (hereinafter called "batch"), comprising adding a moisture-binding agent to the batch and subsequently mixing the moisture-binding agent and the batch to form a flowable and homogenous powder that is substantially free of unbound moisture.

2. Method of homogenization and analysis for processing noble-metal containing, moisture-containing recycling materials with an unknown noble metal content (hereinafter called "batch"), comprising the steps of
   A) adding a previously known or pre-calculated quantity of a moisture-binding agent to the batch and mixing the moisture-binding agent and the batch to form a flowable and homogenous powder that is substantially free of unbound moisture; then
   B) taking one or several samples,
   C) drying the sample(s), and
   D) optionally dividing the sample(s), and
   E) conducting an analysis of the sample(s) and calculating the noble metal content of the batch on the basis of the sample analysis and the known or pre-calculated quantity of the moisture-binging agent.

3. Method according to claim 1, wherein the moisture-binding agent is a water-binding agent.

4. Method according to claim 3, wherein the water-binding agent is an organic polymer.

5. Method according to claim 4, wherein the organic polymer is a cross-linked polyacrylate.

6. Method according to claim 3, wherein the water-binding agent is a super-absorber.

7. Method according to claim 1, wherein the moisture-binding agent is activated carbon.

8. Method according to claim 1, wherein the moisture-binding agent is a mixture of activated carbon and a super-absorber.

9. Method according to claim 1, wherein the batch consists of noble metal-containing, spent catalysts.

10. Method according to claim 1, wherein the batch has a moisture content of 20-80% by weight.

11. Method according to claim 2, wherein a representative part of the batch is removed in step B.

12. Method according to claim 2, wherein individual samples are taken during the mixing process and the combined individual samples are subsequently dried in order to be subsequently mixed and divided into further individual samples.

13. Method according to claim 12, wherein the combined individual samples after drying are mixed and divided by means of a rotary divider.

14. Method according to claim 9, wherein the spent catalyst contains noble metals on activated carbon.

15. Method according to claim 2, wherein the dried sample from step C is a solid with a particle size of <500 μm.

16. Method according to claim 2, wherein the dried sample from step C is a solid with a particles size of <100 μm.

17. Method according to claim 1, wherein the mixing takes place in an intensive mixer with cutting rotors thereby comminuting the mixture.

* * * * *